(12) United States Patent
Nita et al.

(10) Patent No.: US 8,641,630 B2
(45) Date of Patent: Feb. 4, 2014

(54) CONNECTOR FOR SECURING ULTRASOUND CATHETER TO TRANSDUCER

(75) Inventors: Henry Nita, Redwood Shores, CA (US); Martinos Tran, Tracy, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 229 days.

(21) Appl. No.: 12/831,883

(22) Filed: Jul. 7, 2010

(65) Prior Publication Data

US 2010/0280389 A1 Nov. 4, 2010

Related U.S. Application Data

(63) Continuation of application No. 11/192,749, filed on Jul. 29, 2005, now Pat. No. 7,758,510, which is a continuation of application No. 10/666,459, filed on Sep. 19, 2003, now Pat. No. 6,942,620.

(51) Int. Cl.
*A61B 8/00* (2006.01)

(52) U.S. Cl.
USPC .............................. 600/466; 601/2; 600/459

(58) Field of Classification Search
USPC .................... 600/300, 437–461; 604/19, 20
See application file for complete search history.

(56) References Cited

U.S. PATENT DOCUMENTS

| | | | |
|---|---|---|---|
| 3,433,226 A | 3/1969 | Boyd | |
| 3,565,062 A | 2/1971 | Kuris | |
| 3,631,848 A | 1/1972 | Muller | |
| 3,719,737 A | 3/1973 | Vaillancourt et al. | |
| 3,823,717 A | 7/1974 | Pohlman et al. | |
| 3,896,811 A | 7/1975 | Storz | |
| 4,016,882 A | 4/1977 | Broadwin et al. | |
| 4,033,331 A | 7/1977 | Guss et al. | |
| 4,136,700 A | 1/1979 | Broadwin et al. | |
| 4,337,090 A | 6/1982 | Harrison | |

(Continued)

FOREIGN PATENT DOCUMENTS

| | | |
|---|---|---|
| DE | 2256127 | 5/1974 |
| DE | 2438648 | 2/1976 |

(Continued)

OTHER PUBLICATIONS

Siegel, et al., "In Vivo Ultrasound Arterial Recanalization of Atherosclerotic Total Occlusions", Journal of the American College of Cardiology, Feb. 1990, vol. 15, No. 2, pp. 345-351.

(Continued)

*Primary Examiner* — Jonathan Cwern
(74) *Attorney, Agent, or Firm* — Knobbe Martens Olson & Bear LLP

(57) ABSTRACT

An ultrasound system has an ultrasound transducer having a transducer housing and a horn provided at the distal end of the transducer housing, an ultrasound transmission member, a sonic connector that is connected to the horn and the proximal end of the ultrasound transmission member, and a catheter knob having a proximal end that is coupled to the distal end of the transducer housing. The catheter knob has a proximal bore that houses the sonic connector. The system also includes a nesting piece that is retained inside the proximal bore of the catheter knob. The nesting piece can be moved from a first position where the sonic connector is received inside the nesting piece to a second position where the sonic connector is separated from the nesting piece when ultrasound energy is being propagated through the ultrasound transmission member.

10 Claims, 7 Drawing Sheets

(56) References Cited

U.S. PATENT DOCUMENTS

| | | | |
|---|---|---|---|
| 4,368,410 | A | 1/1983 | Hance |
| 4,417,578 | A | 11/1983 | Banko |
| 4,425,115 | A | 1/1984 | Wuchinich |
| 4,486,680 | A | 12/1984 | Bonnet et al. |
| 4,505,767 | A | 3/1985 | Quin |
| 4,545,767 | A | 10/1985 | Suzuki et al. |
| 4,565,589 | A | 1/1986 | Harrison |
| 4,565,787 | A | 1/1986 | Bossle et al. |
| 4,572,184 | A | 2/1986 | Stohl et al. |
| 4,664,112 | A | 5/1987 | Kensey et al. |
| 4,665,906 | A | 5/1987 | Jervis |
| 4,679,558 | A | 7/1987 | Kensey et al. |
| 4,700,705 | A | 10/1987 | Kensey et al. |
| 4,721,117 | A | 1/1988 | Mar et al. |
| 4,750,902 | A | 6/1988 | Wuchinich et al. |
| 4,808,153 | A | 2/1989 | Parisi |
| 4,811,743 | A | 3/1989 | Stevens |
| 4,827,911 | A | 5/1989 | Broadwin et al. |
| 4,838,853 | A | 6/1989 | Parisi |
| 4,854,325 | A | 8/1989 | Stevens |
| 4,870,953 | A | 10/1989 | Donmicheal |
| 4,886,060 | A | 12/1989 | Wiksell |
| 4,920,954 | A | 5/1990 | Alliger |
| 4,923,462 | A | 5/1990 | Stevens |
| 4,924,863 | A | 5/1990 | Sterzer |
| 4,931,047 | A | 6/1990 | Broadwin et al. |
| 4,936,281 | A | 6/1990 | Stasz |
| 4,936,845 | A | 6/1990 | Stevens |
| 5,000,185 | A | 3/1991 | Yock |
| 5,015,227 | A | 5/1991 | Broadwin et al. |
| 5,026,384 | A | 6/1991 | Farr et al. |
| 5,046,503 | A | 9/1991 | Schneiderman |
| 5,053,008 | A | 10/1991 | Bajaj |
| 5,058,570 | A | 10/1991 | Idemoto et al. |
| 5,076,276 | A | 12/1991 | Sakurai |
| 5,091,205 | A | 2/1992 | Fan |
| 5,100,423 | A | 3/1992 | Fearnot |
| 5,109,859 | A | 5/1992 | Jenkins |
| 5,114,414 | A | 5/1992 | Buchbinder |
| 5,116,350 | A | 5/1992 | Stevens |
| 5,127,917 | A | 7/1992 | Niederhauser et al. |
| 5,156,143 | A | 10/1992 | Bocquet et al. |
| 5,163,421 | A | 11/1992 | Bernstein |
| 5,171,216 | A | 12/1992 | Dasse et al. |
| 5,180,363 | A | 1/1993 | Idemoto et al. |
| 5,183,470 | A | 2/1993 | Wettermann |
| 5,195,955 | A | 3/1993 | Don Michael |
| 5,215,614 | A | 6/1993 | Wijkamp et al. |
| 5,221,255 | A | 6/1993 | Mahurkar et al. |
| 5,226,421 | A | 7/1993 | Frisbie et al. |
| 5,234,416 | A | 8/1993 | Macaulay et al. |
| 5,238,004 | A | 8/1993 | Sahatjian et al. |
| 5,242,385 | A | 9/1993 | Strukel |
| 5,243,997 | A | 9/1993 | Uflacker et al. |
| 5,248,296 | A | 9/1993 | Alliger |
| 5,255,669 | A | 10/1993 | Kubota et al. |
| 5,267,954 | A | 12/1993 | Nita |
| 5,269,291 | A | 12/1993 | Carter |
| 5,269,297 | A | 12/1993 | Weng et al. |
| 5,269,793 | A | 12/1993 | Simpson |
| 5,287,858 | A | 2/1994 | Hammerslag et al. |
| 5,290,229 | A | 3/1994 | Paskar |
| 5,304,115 | A | 4/1994 | Pflueger |
| 5,304,131 | A | 4/1994 | Paskar |
| 5,312,328 | A | 5/1994 | Nita et al. |
| 5,318,014 | A | 6/1994 | Carter |
| 5,318,570 | A | 6/1994 | Hood et al. |
| 5,324,255 | A | 6/1994 | Passafaro et al. |
| 5,324,260 | A | 6/1994 | O'neill et al. |
| 5,325,860 | A | 7/1994 | Seward et al. |
| 5,326,342 | A | 7/1994 | Pflueger et al. |
| 5,341,818 | A | 8/1994 | Abrams et al. |
| 5,342,292 | A | 8/1994 | Nita et al. |
| 5,344,395 | A | 9/1994 | Whalen et al. |
| 5,346,502 | A | 9/1994 | Estabrook et al. |
| 5,362,309 | A | 11/1994 | Carter |
| 5,368,557 | A | 11/1994 | Nita |
| 5,368,558 | A | 11/1994 | Nita |
| 5,376,084 | A | 12/1994 | Bacich et al. |
| 5,378,234 | A | 1/1995 | Hammerslag et al. |
| 5,380,274 | A | 1/1995 | Nita |
| 5,380,316 | A | 1/1995 | Aita et al. |
| 5,382,228 | A | 1/1995 | Nita et al. |
| 5,383,460 | A | 1/1995 | Jang et al. |
| 5,389,096 | A | 2/1995 | Aita et al. |
| 5,391,144 | A | 2/1995 | Sakurai et al. |
| 5,397,293 | A | 3/1995 | Alliger |
| 5,397,301 | A | 3/1995 | Pflueger et al. |
| 5,405,318 | A | 4/1995 | Nita |
| 5,409,483 | A | 4/1995 | Campbell et al. |
| 5,417,672 | A * | 5/1995 | Nita et al. .................. 604/533 |
| 5,417,703 | A | 5/1995 | Brown et al. |
| 5,421,923 | A | 6/1995 | Clarke et al. |
| 5,427,118 | A | 6/1995 | Nita et al. |
| 5,431,168 | A | 7/1995 | Webster, Jr. |
| 5,431,663 | A | 7/1995 | Carter |
| 5,443,078 | A | 8/1995 | Uflacker |
| 5,447,509 | A | 9/1995 | Mills et al. |
| 5,449,369 | A | 9/1995 | Imran |
| 5,451,209 | A | 9/1995 | Ainsworth et al. |
| 5,465,733 | A | 11/1995 | Hinohara et al. |
| 5,474,531 | A | 12/1995 | Carter |
| 5,480,379 | A | 1/1996 | La Rosa |
| 5,484,398 | A | 1/1996 | Stoddard |
| 5,487,757 | A | 1/1996 | Truckai et al. |
| 5,507,738 | A | 4/1996 | Ciervo |
| 5,516,043 | A | 5/1996 | Manna et al. |
| 5,527,273 | A | 6/1996 | Manna et al. |
| 5,540,656 | A | 7/1996 | Pflueger et al. |
| 5,542,917 | A | 8/1996 | Nita et al. |
| 5,597,497 | A | 1/1997 | Dean et al. |
| 5,597,882 | A | 1/1997 | Schiller et al. |
| 5,607,421 | A | 3/1997 | Jeevanandam et al. |
| 5,611,807 | A | 3/1997 | O'Boyle |
| 5,618,266 | A | 4/1997 | Liprie |
| 5,626,593 | A | 5/1997 | Imran |
| 5,649,935 | A | 7/1997 | Kremer et al. |
| 5,658,282 | A | 8/1997 | Daw et al. |
| 5,695,460 | A | 12/1997 | Siegel et al. |
| 5,695,507 | A | 12/1997 | Auth et al. |
| 5,715,825 | A | 2/1998 | Crowley |
| 5,720,724 | A | 2/1998 | Ressemann et al. |
| 5,728,062 | A | 3/1998 | Brisken |
| 5,738,100 | A | 4/1998 | Yagami et al. |
| 5,797,876 | A | 8/1998 | Spears et al. |
| 5,816,923 | A | 10/1998 | Milo et al. |
| 5,827,203 | A | 10/1998 | Nita |
| 5,830,222 | A | 11/1998 | Makower |
| 5,895,397 | A | 4/1999 | Jang et al. |
| 5,902,287 | A | 5/1999 | Martin |
| 5,916,192 | A | 6/1999 | Nita et al. |
| 5,916,912 | A | 6/1999 | Ames et al. |
| 5,935,142 | A | 8/1999 | Hood |
| 5,937,301 | A | 8/1999 | Gardner et al. |
| 5,944,737 | A | 8/1999 | Tsonton et al. |
| 5,957,882 | A | 9/1999 | Nita et al. |
| 5,957,899 | A | 9/1999 | Spears et al. |
| 5,964,223 | A | 10/1999 | Baran |
| 5,967,984 | A | 10/1999 | Chu et al. |
| 5,971,949 | A | 10/1999 | Levin et al. |
| 5,976,119 | A | 11/1999 | Spears et al. |
| 5,989,208 | A | 11/1999 | Nita |
| 5,997,497 | A | 12/1999 | Nita et al. |
| 6,004,280 | A | 12/1999 | Buck et al. |
| 6,007,499 | A | 12/1999 | Martin et al. |
| 6,007,514 | A | 12/1999 | Nita |
| 6,024,764 | A | 2/2000 | Schroeppel |
| 6,029,671 | A | 2/2000 | Stevens et al. |
| 6,030,357 | A | 2/2000 | Daoud et al. |
| 6,051,010 | A | 4/2000 | DiMatteo et al. |
| 6,113,558 | A | 9/2000 | Rosenschein et al. |
| 6,123,698 | A | 9/2000 | Spears et al. |
| 6,149,596 | A | 11/2000 | Bancroft |
| 6,165,127 | A | 12/2000 | Crowley |

(56) References Cited

U.S. PATENT DOCUMENTS

| | | |
|---|---|---|
| 6,165,188 A | 12/2000 | Saadat et al. |
| 6,179,809 B1 | 1/2001 | Khairkhahan et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,315,741 B1 | 11/2001 | Martin et al. |
| 6,379,378 B1 | 4/2002 | Werneth et al. |
| 6,387,109 B1 | 5/2002 | Davison et al. |
| 6,394,956 B1 | 5/2002 | Chandrasekaran et al. |
| 6,398,736 B1 | 6/2002 | Seward |
| 6,416,533 B1 | 7/2002 | Gobin et al. |
| 6,423,026 B1 | 7/2002 | Gesswein et al. |
| 6,433,464 B2 | 8/2002 | Jones |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,491,707 B2 | 12/2002 | Makower |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,589,253 B1 | 7/2003 | Cornish et al. |
| 6,596,235 B2 | 7/2003 | Divino, Jr. et al. |
| 6,616,617 B1 | 9/2003 | Ferrera et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,702,748 B1 | 3/2004 | Nita et al. |
| 6,702,750 B2 | 3/2004 | Yock |
| 6,719,725 B2 | 4/2004 | Milo et al. |
| 6,733,451 B2 | 5/2004 | Rabiner et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,220,233 B2 | 5/2007 | Nita et al. |
| 7,267,650 B2 | 9/2007 | Chow et al. |
| 7,335,180 B2 | 2/2008 | Nita et al. |
| 7,384,407 B2 | 6/2008 | Rodriguez et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,929 B2 | 11/2009 | Nita et al. |
| 2002/0049402 A1 | 4/2002 | Peacock, III et al. |
| 2002/0077643 A1 | 6/2002 | Rabiner et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0138570 A1 | 7/2004 | Nita et al. |
| 2004/0167507 A1 | 8/2004 | Nita et al. |
| 2004/0204670 A1 | 10/2004 | Nita et al. |
| 2005/0113688 A1 | 5/2005 | Nita et al. |
| 2005/0215946 A1 | 9/2005 | Hansmann et al. |
| 2005/0222557 A1 | 10/2005 | Baxter et al. |
| 2005/0228286 A1 | 10/2005 | Messerly et al. |
| 2006/0206039 A1 | 9/2006 | Wilson et al. |
| 2006/0264809 A1 | 11/2006 | Hansmann et al. |
| 2007/0037119 A1 | 2/2007 | Pal et al. |
| 2007/0260172 A1 | 11/2007 | Nita |
| 2008/0108937 A1 | 5/2008 | Nita |
| 2008/0221506 A1 | 9/2008 | Rodriguez et al. |
| 2008/0228111 A1 | 9/2008 | Nita |
| 2008/0287804 A1 | 11/2008 | Nita |
| 2011/0130834 A1 | 6/2011 | Wilson et al. |

FOREIGN PATENT DOCUMENTS

| | | |
|---|---|---|
| DE | 3821836 | 1/1990 |
| DE | 8910040 | 1/1990 |
| DE | 4042435 | 8/1991 |
| EP | 0005719 | 12/1979 |
| EP | 0316789 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0820728 | 1/1998 |
| GB | 1106957 | 3/1968 |
| JP | 01099547 | 4/1989 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| WO | WO8705739 | 9/1987 |
| WO | WO8906515 | 7/1989 |
| WO | WO9001300 | 2/1990 |
| WO | WO9004362 | 5/1990 |
| WO | WO9107917 | 6/1991 |
| WO | WO9211815 | 7/1992 |
| WO | WO9308750 | 5/1993 |
| WO | WO9316646 | 9/1993 |
| WO | WO9412140 | 6/1994 |
| WO | WO9414382 | 7/1994 |
| WO | WO9508954 | 4/1995 |
| WO | WO9509571 | 4/1995 |
| WO | WO 95/15192 | 6/1995 |
| WO | WO9635469 | 11/1996 |
| WO | WO9705739 | 2/1997 |
| WO | WO 97/21462 | 6/1997 |
| WO | WO9745078 | 12/1997 |
| WO | WO9827874 | 7/1998 |
| WO | WO 98/52637 | 11/1998 |
| WO | WO9925412 | 5/1999 |
| WO | WO0053341 A1 | 9/2000 |
| WO | WO00/67830 | 11/2000 |
| WO | WO2004012609 | 2/2004 |
| WO | WO2004112888 | 12/2004 |
| WO | WO 2006/049593 | 5/2006 |

OTHER PUBLICATIONS

(56) References Cited

OTHER PUBLICATIONS

Extended European Search Report dated Mar. 5, 2012 for European Application No. 12153606.4.

Health Care Without Harm [report], Non-Incineration Medical Waste Treatment Technologies, "Irradiation, biological, and other technologies: E-beam, biological, and sharps treatment systems", Chapter 9., Aug. 2001, pp. 69-74.

* cited by examiner

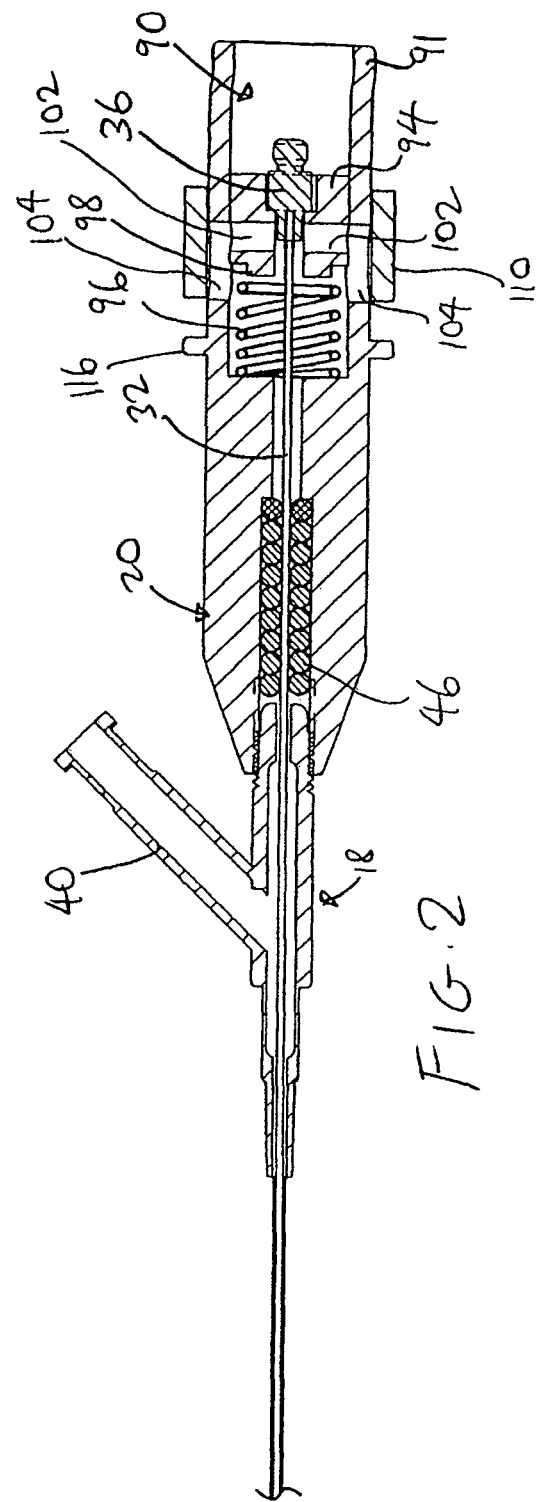

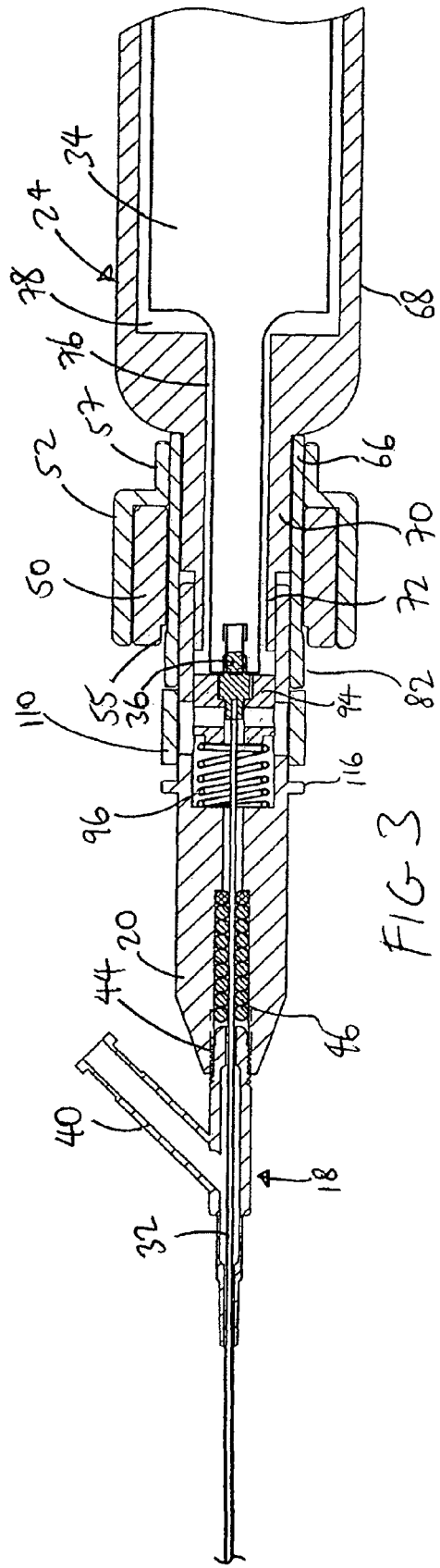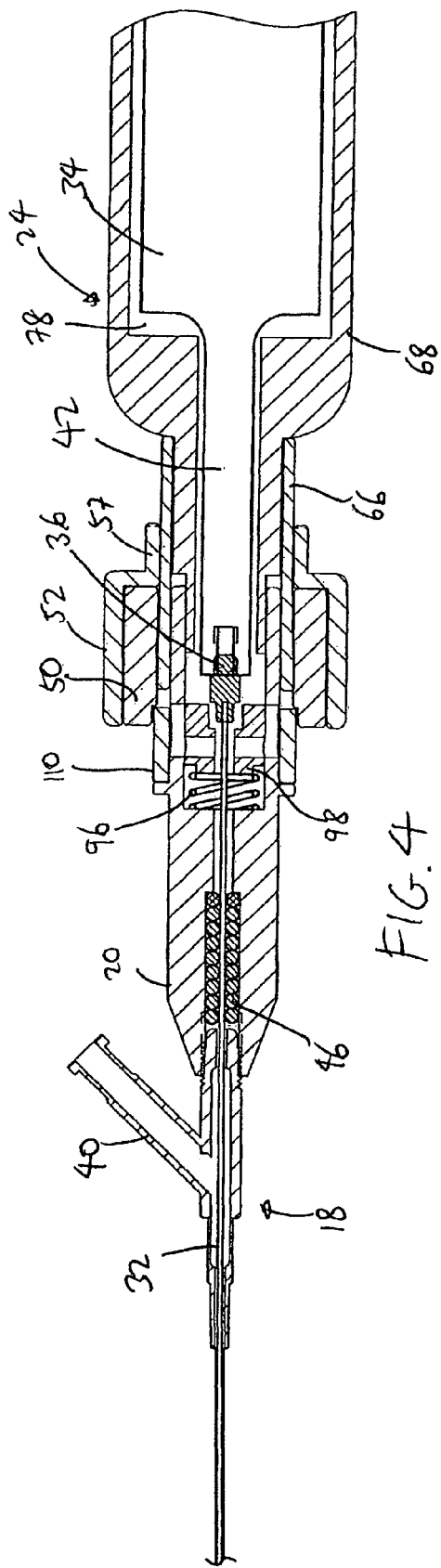

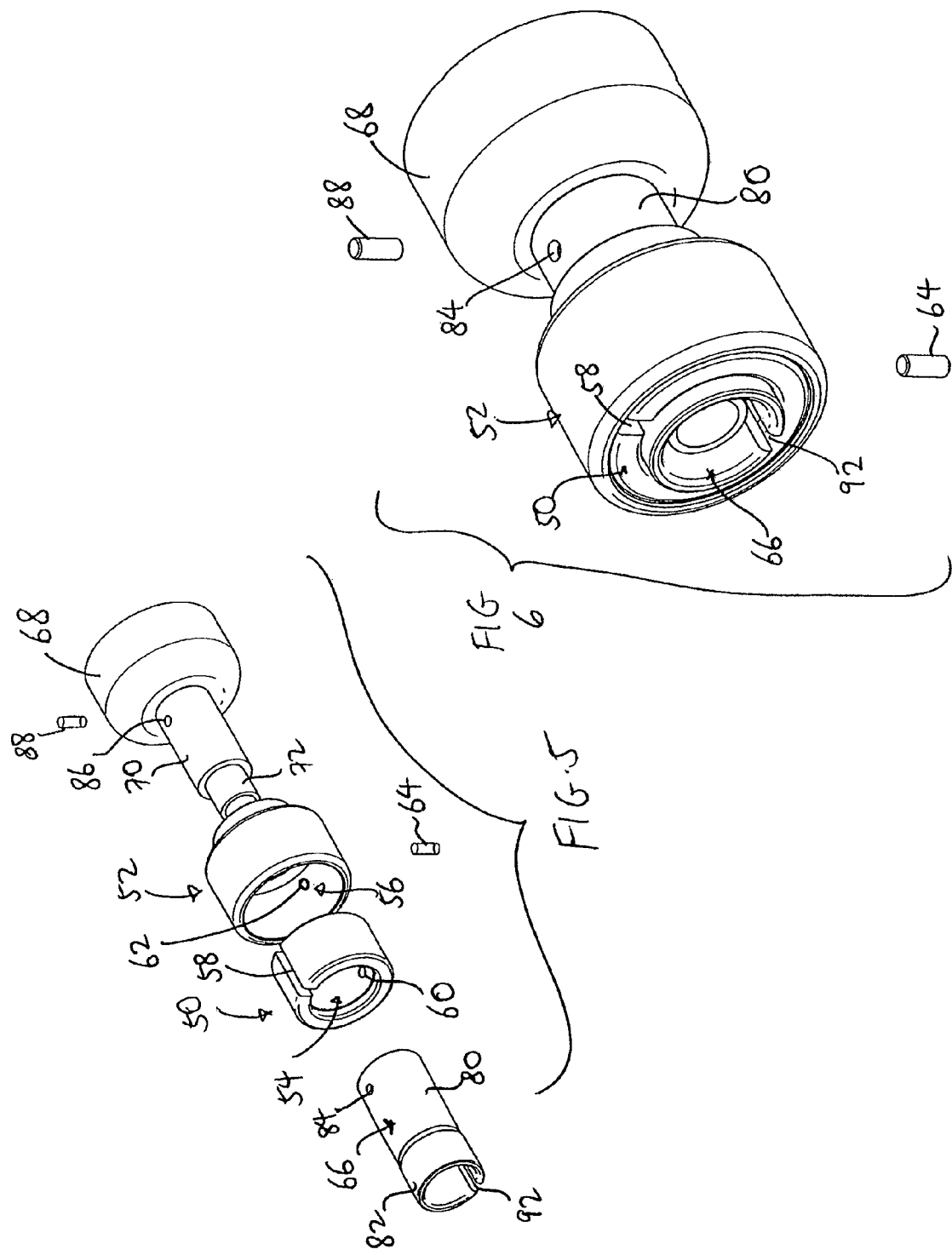

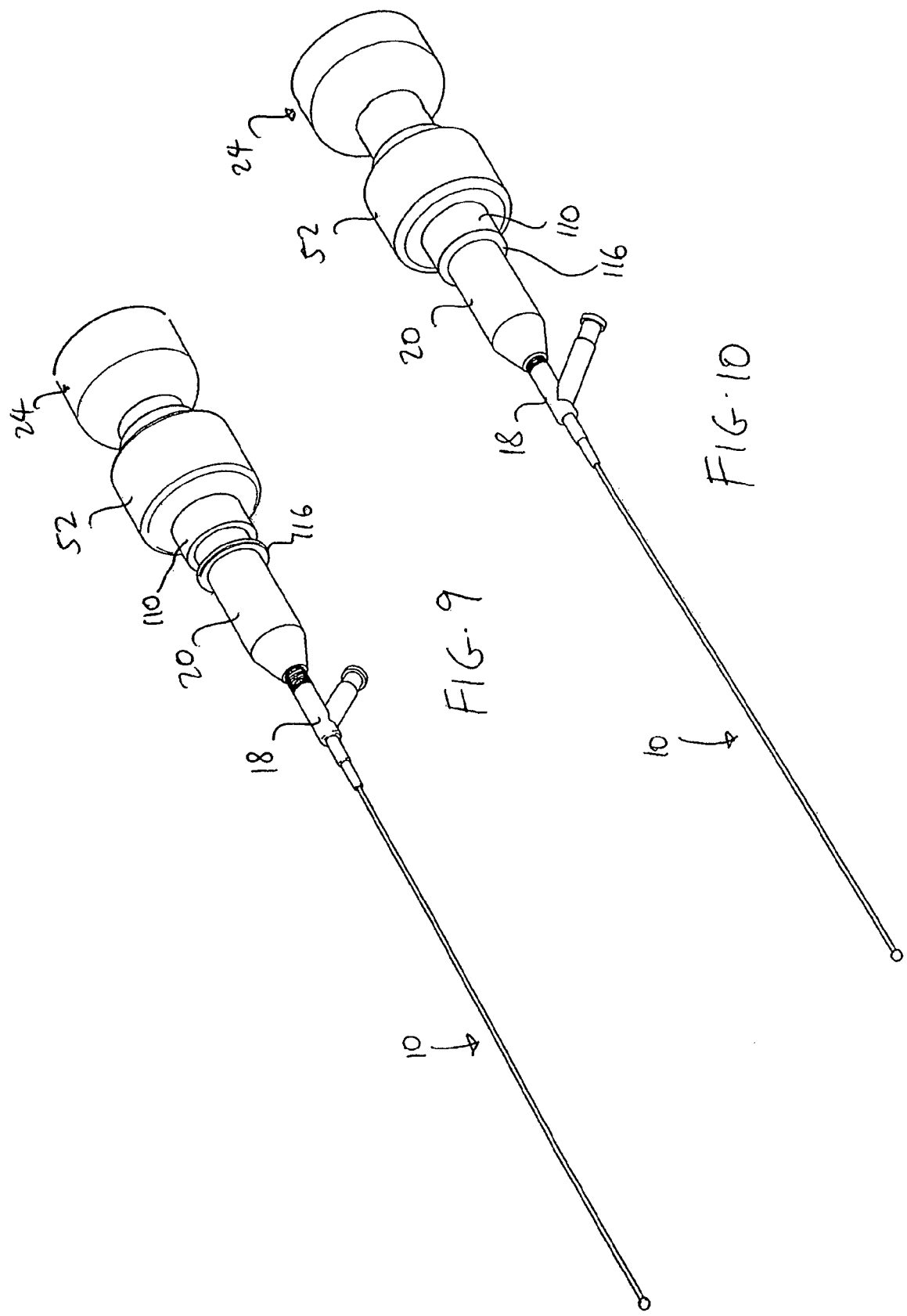

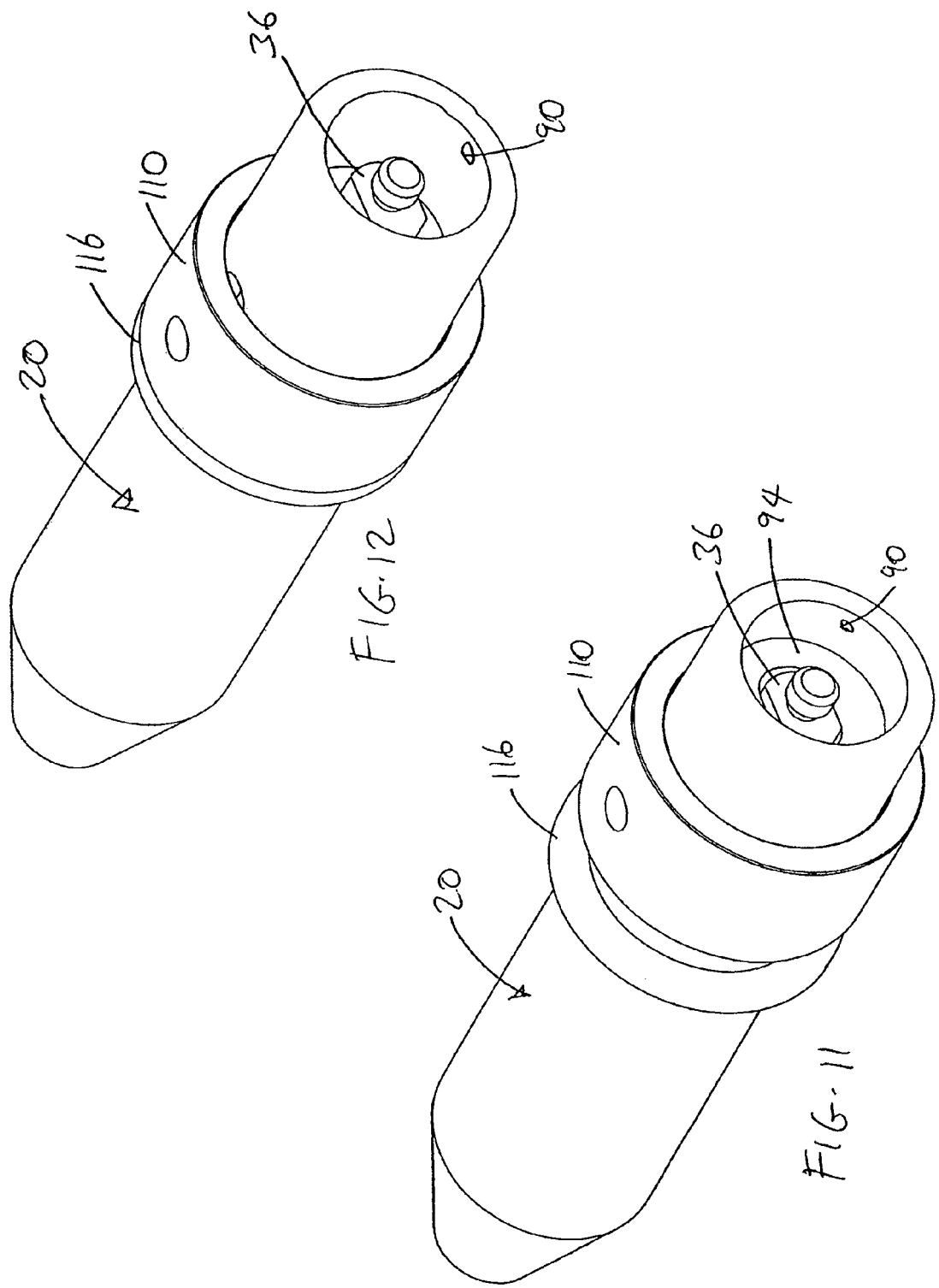

CONNECTOR FOR SECURING ULTRASOUND CATHETER TO TRANSDUCER

CROSS-REFERENCE TO RELATED APPLICATIONS

This is a continuation of Ser. No. 11/192,749, filed Jul. 29, 2005, entitled "Connector for Securing Ultrasound Catheter to Transducer", which is a continuation of Ser. No. 10/666,459, filed Sep. 19, 2003, entitled "Connector for Securing Ultrasound Catheter to Transducer", now U.S. Pat. No. 6,942,620, each of which is incorporated by this reference as though set forth fully herein.

BACKGROUND OF THE INVENTION

1. Field of the Invention

The present invention pertains to medical equipment, and more particularly, to a device and method for attaching an ultrasound catheter to an ultrasound transducer which prevents frequency shifts and minimizes the mechanical impact of the handling connection area during a medical procedure.

2. Description of the Related Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, require the use of relatively small diameter ultrasound catheters which are sufficiently small and flexible to undergo transluminal advancement through the tortuous vasculature of the aortic arch and coronary tree. These ultrasound catheters incorporate a very small diameter ultrasound transmission member which extends through such catheters. The proximal end of the ultrasound transmission member is typically connected to an ultrasound transducer via a sonic connector.

The attachment of the ultrasound transmission member to an ultrasound transducer plays a very important role in ultrasound energy propagation. The attachment region needs to be accurately aligned and free of mechanical stress and other interfaces. For example, undesirable stress at the attachment region can be caused by pressing upon, pushing, pulling, torquing, bending or bumping the attachment region during use of the ultrasound catheter. In addition, it is preferable for the sonic connector to be free from any interface (i.e., contact) with any other component during energy transmission. Otherwise, such stresses and interfaces can negatively impact the propagation of ultrasound energy through the ultrasound transmission member. Contact of the sonic connector with any other part of the catheter housing during the delivery of ultrasound energy might also cause a shift in frequency and impact performance.

Thus, there still exists a need for an improved connection of the proximal end of the ultrasound transmission member to an ultrasound transducer.

SUMMARY OF THE INVENTION

It is an object of the present invention to provide an improved connection between the ultrasound catheter and the ultrasound transducer.

It is yet another object of the present invention to improve the propagation of ultrasound energy by limiting and minimizing the impact of undesirable external forces.

In order to accomplish the objects of the present invention, there is provided an ultrasound system and method of using the ultrasound system during a medical procedure. The ultrasound system has an ultrasound transducer having a transducer housing and a horn provided at the distal end of the transducer housing, an ultrasound transmission member, a sonic connector that is connected to the horn and the proximal end of the ultrasound transmission member, and a catheter knob having a proximal end that is coupled to the distal end of the transducer housing. The catheter knob has a proximal bore that houses the sonic connector. The system also includes a nesting piece that is retained inside the proximal bore of the catheter knob. The nesting piece can be moved from a first position where the sonic connector is received inside the nesting piece to a second position where the sonic connector is separated from the nesting piece when ultrasound energy is being propagated through the ultrasound transmission member.

BRIEF DESCRIPTION OF THE DRAWINGS

FIG. 2 is a cross-sectional view of the Y-connector and catheter knob of the system of FIG. 1.

FIG. 3 is a cross-sectional view of the Y-connector, the catheter knob, the slide collar assembly and the transducer housing of the system of FIG. 1 with the slide collar assembly in the non-supporting position.

FIG. 4 is a cross-sectional view of the Y-connector, the catheter knob, the slide collar assembly and the transducer housing of the system of FIG. 1 with the slide collar assembly in the supporting position.

FIG. 5 is an exploded perspective view of some of the elements of the slide collar assembly of the system of FIG. 1.

FIG. 6 is an assembled perspective view of the elements of FIG. 5.

FIG. 9 is a perspective view of the system of FIG. 1 with the slide collar assembly in the non-supporting position.

FIG. 10 is a perspective view of the system of FIG. 1 with the slide collar assembly in the supporting position.

FIG. 11 is a perspective view of the catheter knob of the system of FIG. 1 with the slide collar assembly in the non-supporting position.

FIG. 12 is a perspective view of the catheter knob of the system of FIG. 1 with the slide collar assembly in the supporting position.

DETAILED DESCRIPTION OF THE PREFERRED EMBODIMENT

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
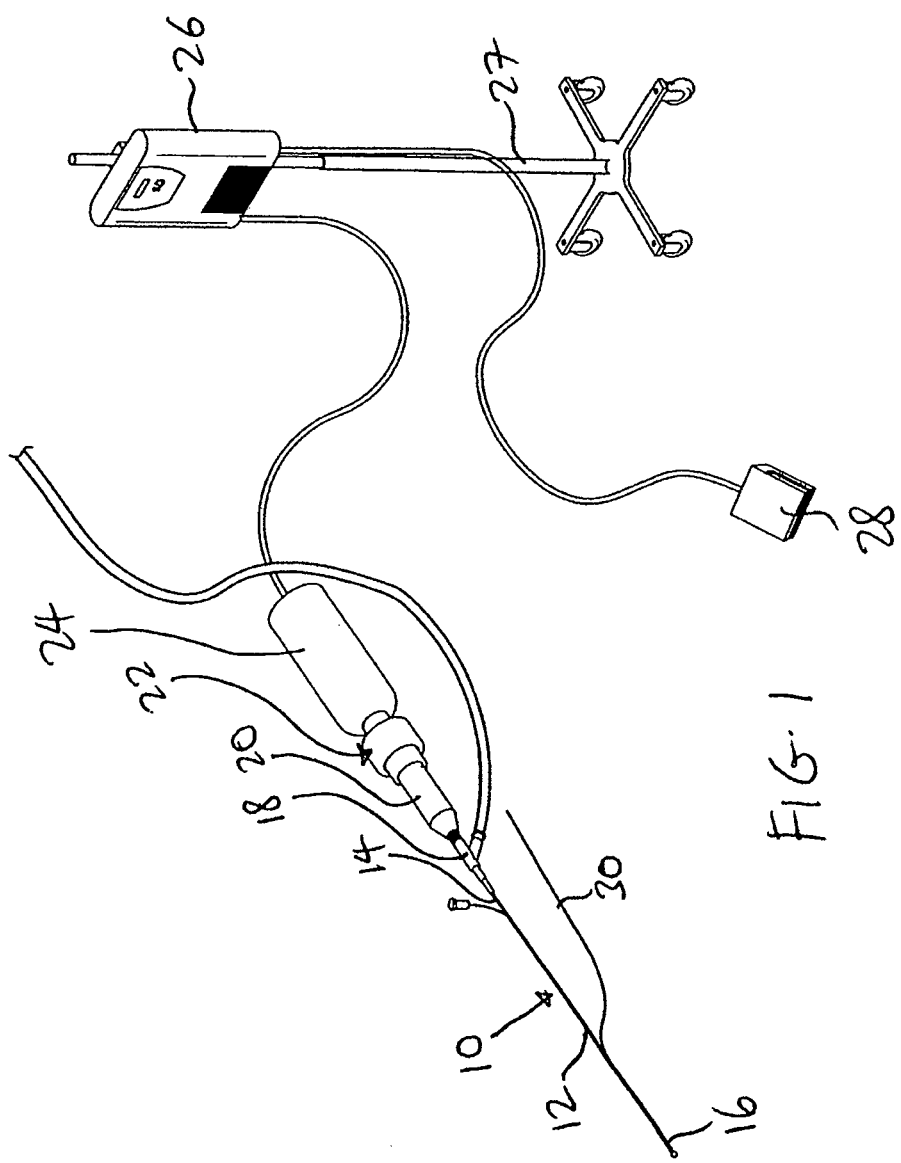
FIG. 1 is a perspective view of an ultrasound system according to one embodiment of the present invention.

FIG. 1 illustrates an ultrasound system according to the present invention for use in ablating and removing occlusive material inside the vessel of an animal or human being. The ultrasound system includes an ultrasonic catheter device 10 which has an elongate catheter body 12 having a proximal end 14, a distal end 16, and defining at least one lumen extending longitudinally therethrough. The ultrasound catheter device 10 is operatively coupled at its proximal end 14, by way of a Y-connector 18, a catheter knob 20, and a slide collar assembly 22, to an ultrasound transducer housing 24 As shown in FIGS. 3-4, an ultrasound transducer 34 is housed inside the transducer housing 24. The ultrasound transducer 34 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 34, which converts the electrical signal to ultrasound energy. Such ultrasound energy subsequently passes through the catheter device 10 and is delivered to the distal end 16.

Referring also to FIGS. 2-4, an ultrasound transmission member 32 extends through the lumen of the catheter 10 from the distal end 16 to the proximal end 14. The ultrasound transducer 34 is coupled via a sonic connector 36 (described in greater detail below) to the ultrasound transmission member 32, so that the ultrasound energy can be passed through the sonic connector 36 and the ultrasound transmission member 32 to be delivered to the distal end 16 of the catheter 10. A guidewire 30, which can be any conventional monorail or over-the-wire guidewire, may be utilized in conjunction with the catheter 10 in a manner that is well-known in the catheter art.

The frontal portion of the Y-connector 18 is connected to the proximal end 12 of the catheter 10 using techniques that are well-known in the catheter art. An injection pump (not shown) or IV bag (not shown) can be connected, by way of an infusion tube (not shown), to an infusion port or sidearm 40 of the Y-connector 18. The injection pump can be used to infuse coolant fluid (e.g., 0.9% NaCl solution) into and/or through the lumen of the catheter 10. Such flow of coolant fluid may be utilized to prevent overheating of the ultrasound transmission member 32 extending longitudinally through the lumen of the catheter 10. Such flow of the coolant fluid through the lumen of the catheter 10 serves to bathe the outer surface of the ultrasound transmission member 32, thereby providing for an equilibration of temperature between the coolant fluid and the ultrasound transmission member 32. Thus, the temperature and/or flow rate of coolant fluid may be adjusted to provide adequate cooling and/or other temperature control of the ultrasound transmission member 32. In addition to the foregoing, the injection pump may be utilized to infuse a radiographic contrast medium into the catheter 10 for purposes of imaging.

Examples of iodinated radiographic contrast media which may be selectively infused into the catheter 10 via the injection pump are commercially available as Angiovist 370 from Berlex Labs, Wayne, N.J. and Hexabrix from Malinkrodt, St. Louis, Mo.

The proximal end of the ultrasound transmission member 32 is attached to the sonic connector 36 which is configured to effect operative and removable attachment of the proximal end of the ultrasound transmission member 32 to the distal horn 42 of the ultrasound transducer 34. The sonic connector 36 is preferably configured and constructed to permit passage of ultrasound energy through the ultrasound transmission member 32 with minimal lateral side-to-side movement of the ultrasound transmission member 32 while, at the same time, permitting unrestricted longitudinal forward/backward vibration or movement of the ultrasound transmission member 32.

The ultrasound transmission member 32 may be formed of any material capable of effectively transmitting the ultrasonic energy from the ultrasound transducer 34 to the distal end 16 of the catheter 10, including but not necessarily limited to metal, plastic, hard rubber, ceramic, fiber optics, crystal, polymers, and/or composites thereof In accordance with one aspect of the invention, all or a portion of the ultrasound transmission member 32 may be formed of one or more materials which exhibit super-elasticity. Such materials should preferably exhibit super-elasticity consistently within the range of temperatures normally encountered by the ultrasound transmission member 32 during operation of the catheter 10. Specifically, all or part of the ultrasound transmission member 32 may be formed of one or more metal alloys known as "shape memory alloys". Such super-elastic metal alloys are well-known in the art and will not be described in any further detail herein.

The proximal end of the Y-connector 18 is attached to the distal end of the catheter knob 20 by threadably engaging the proximal end of the Y-connector 18 inside a threaded distal bore 44 at the distal end of the catheter knob 20. O-rings 46 are provided in the threaded distal bore 44 to minimize transverse vibrations. The proximal end of the catheter knob 20 receives the extension 70 of the transducer housing 24 and is supported by the slide collar assembly 22. The slide collar assembly 22 is positioned over the distal end of the transducer housing 24, and has a non-supporting position where the slide collar assembly 22 is retracted towards the transducer housing 24; and has a supporting position where the slide collar assembly 22 is extended to cover at least a portion of the catheter knob 20. Thus, the slide collar assembly 22 functions as a support member that is disposed on the transducer housing 24 to support at least a portion of the catheter knob 20.

Referring also to FIGS. 5 and 6, the slide collar assembly 22 has an inner ring 50 (also referred to as collar 50) and an outer ring 52 (also referred to as collar 52). The inner ring 50 has a bore 54 and a longitudinal slit 58 that extends through the length of the inner ring 50. The distal portion of the bore 54 can be stepped as shown at 55 (see FIG. 3) to function as a pushing surface that pushes a nesting piece 94 (described below) in a distal direction as the inner ring 50 is moved from the non-supporting position to the supporting position. The outer ring 52 also has a bore 56, and has a narrowed proximal end 57. The inner ring 50 is retained inside the bore 56 of the outer ring 52 and abuts the narrowed proximal end 57 which acts as a stop to limit the proximal movement of the inner ring 50. Each of the inner ring 50 and the outer ring 52 has an opening 60 and 62, respectively, that are aligned with each other and that are adapted to receive a locking pin 64. A tubular inner sleeve 66 extends through the inside of the bore 54 of the inner ring 50 to ensleeve the first extension 70 of the transducer housing 24, as explained below. The sleeve 66 has a proximal section 80 and an enlarged distal section 82. The inner ring 50 is normally fitted around the proximal section 80 when the slide collar assembly 22 is in the non-supporting position, but the inner ring 50 is fitted around the distal section 82 when the slide collar assembly 22 is in the supporting position. Thus, providing the distal section 82 in an enlarged configuration allows for the inner ring 50 to achieve a friction-fit with the distal section 82, while the inner ring 50 experiences a loose fit over the proximal section 80.

The transducer housing 24 has a cylindrical wall 68 having a distal extension that comprises two stepped cylindrical extensions 70 and 72 extending from the distal end of the cylindrical wall 68. The first extension 70 is attached to the distal end of the cylindrical wall 68, and has a greater outer diameter than the second extension 72 that is attached to the distal end of the first extension 70. A throughbore 76 extends from the hollow interior 78 of the cylindrical wall 68 and through the extensions 70 and 72. The throughbore 76 can have the same diameter throughout its length. The second extension 72 is adapted to be received inside the proximal bore 90 of the catheter knob 20, while the first extension 70 is received inside the sleeve 66. In addition, an opening 84 is provided in the proximal section 80 of the sleeve 66 and is aligned with a corresponding opening 86 on the first extension 70, with the openings 84, 86 adapted to receive a locking pin 88 that secures the sleeve 66 to the first extension 70 at a fixed position.

A longitudinal slot 92 is provided on the sleeve 66. When the slide collar assembly 22 is in the non-supporting position (i.e., inner ring 50 positioned over the proximal section 80), the slot 92 is opened. However, when the slide collar assembly 22 is moved to the supporting position, the inner ring 50 is positioned over the distal section 82 and compresses the enlarged distal section 82 to close the slot 92. With the slot 92 closed, the sleeve 66 provides a frictional grip of the proximal end 91 of the catheter knob 20.

Referring now to FIGS. 2-4 and 7-8, the catheter knob 20 has a proximal bore 90 that can be sleeved over the second extension 72 in a manner such that the outer surface of the catheter knob 20 can be substantially flush with the outer surface of the first extension 70 (as best shown in FIGS. 3 and 4). The proximal bore 90 houses the sonic connector 36 and a nesting piece 94. An elastic element 96, such as a spring, is seated in the distal part of the proximal bore 90, and has one end carried on a projection 98 provided at the distal end of the nesting piece 94. The nesting piece 94 has a generally cylindrical configuration and has a receptacle 100 which functions to selectively retain the sonic connector 36, as will be explained in greater detail below. In addition, a control ring 110 is positioned around the outer surface 112 of the catheter knob 20. The control ring 112 cooperates with the nesting piece 94 to move the nesting piece 94 in a reciprocal manner inside the proximal bore 90 of the catheter knob 20, as explained below.

Figure 7:
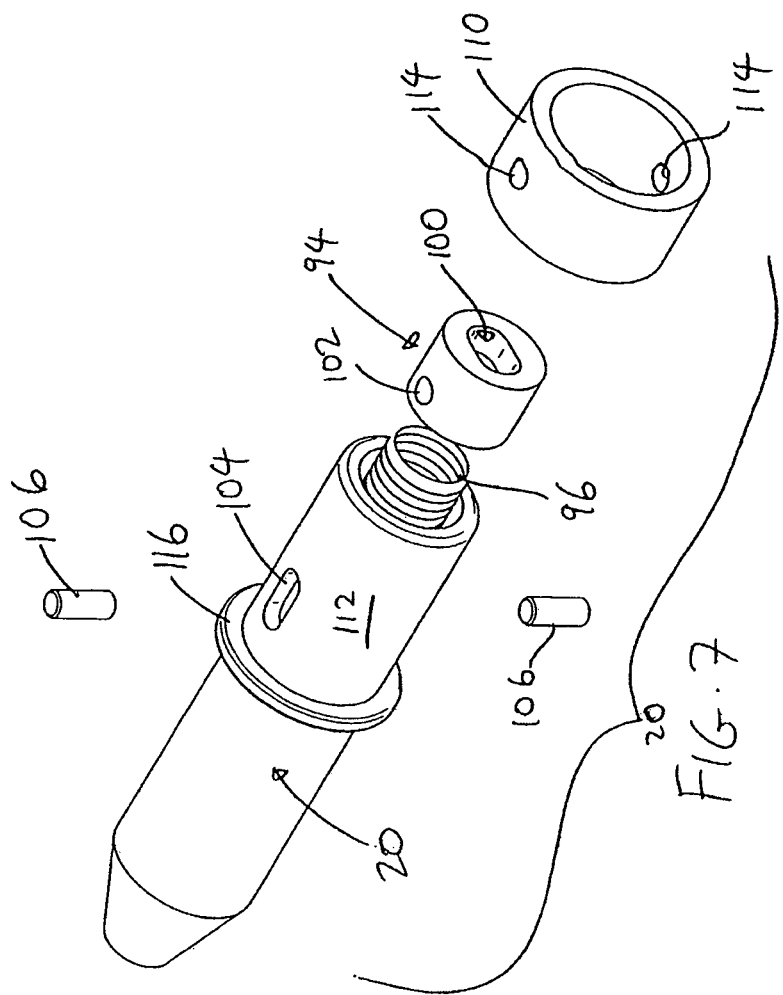
FIG. 7 is an exploded perspective view of the catheter knob of the system of FIG. 1.
Figure 8:
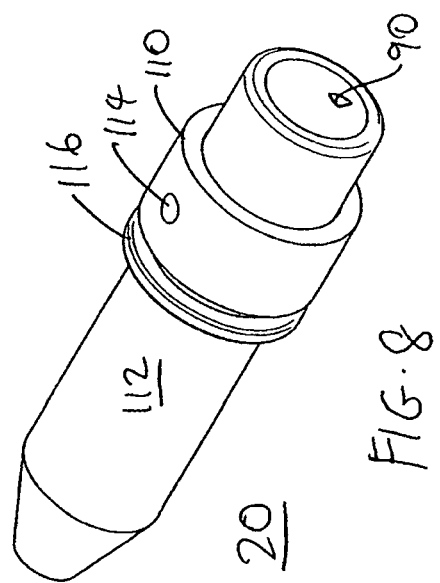
FIG. 8 is an assembled perspective view of the catheter knob of FIG. 7.

The nesting piece 94 has two opposite and aligned openings 102; only the top opening 102 is shown in FIG. 7, but the bottom opening is the same and is aligned on a straight line with the top opening 102. Similarly, the catheter knob 20 has two opposite and aligned channels 104; only the top channel 104 is shown in FIG. 7, but the bottom channel is the same and is aligned on a straight line with the top channel 104. In addition, the control ring 110 has two opposite and aligned openings 114. The channels 104 and the openings 102, 114 are aligned, as best shown in FIGS. 3 and 4. Two opposing pins 106 are provided, with each pin 106 adapted to be fitted inside a corresponding set of channel 104 and openings 102, 114, so as to couple the control ring 110 and the nesting piece 94 as a unitary moving piece. The width of the channels 104 define the distal and proximal limits of movement for the control ring 110 and the nesting piece 94. The catheter knob 20 also has an annular flange 116 provided about its outer surface 112 that also defines the distal limit of the movement of the control ring 110.

In use, the sonic connector 36 is shown in FIGS. 3-4 as connecting the transducer horn 42 (e.g., with a threaded connection) with the ultrasound transmission member 32. The sonic connector 36 is always located at a fixed position inside the proximal bore 90 of the catheter knob 20. When the slide collar assembly 22 is in the non-supporting position shown in FIGS. 3, 9 and 11, the elastic element 96 normally biases the nesting piece 94 in the proximal direction so that the sonic connector 36 is received inside the receptacle 100 of the nesting piece 94 to be supported by the nesting piece 94. The proximal movement of the nesting piece 94 will cause the pins 106 to move in the proximal direction inside the channels 104, thereby causing the control ring 110 to move proximally away from the flange 116. The outer ring 52 and the inner ring 50 are positioned completely over the proximal section 80 of the sleeve 66, with the narrowed proximal end 57 positioned adjacent the cylindrical wall 68 of the transducer housing 24.

When the slide collar assembly 22 is now moved from the non-supporting position to the supporting position shown in FIGS. 4, 10 and 12, the user pushes the outer ring 52 in the distal direction. The step 55 on the distal end of the inner ring 50 engages the proximal end of the control ring 110 and pushes the control ring 110 in the distal direction. Movement of the control ring 110 in the distal direction will cause the pins 106 to move in the distal direction inside the channels 104, thereby causing the nesting piece 94 to counter the bias of the elastic element 96 and move in the distal direction. As the nesting piece 94 moves in the distal direction, the sonic connector 36 becomes free from the receptacle 100 of the nesting bore 94. In addition, the distal movement of the inner ring 50 will cause the inner surface of the inner ring 50 to engage the enlarged distal section 82 of the sleeve 66, which functions to close the slot 92 so as to frictionally grip the proximal portion 91 of the knob 20 when the slide collar assembly 22 is in the supporting position. The flange 116 and the width of the channels 104 function as stops to limit the distal movement of the control ring 110.

In the supporting position, the sonic connector 36 is not supported by the nesting piece 94 so that the sonic connector 36 can be free from any component or material interfaces, thereby promoting improved ultrasound energy propagation. The medical procedure can then be carried out while the slide collar assembly 22 is in the supporting position. Upon completion of the medical procedure, the above-described steps are reversed. In particular, the combined inner and outer rings 50, 52 (slide collar assembly 22) are retracted in the proximal direction so that they are now positioned over the proximal section 80 of the sleeve 66. The bias of the elastic element 96 will push the nesting piece 94 in the proximal direction so that the sonic connector 36 is received inside the receptacle 100 of the nesting piece 94. In addition, the proximal movement of the nesting piece 94 will cause the pins 106 to move in the proximal direction inside the channels 104, thereby causing the control ring 110 to move proximally away from the flange 116. Now, the catheter 10 can be disconnected from the transducer 34.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound system, comprising:
   an ultrasound transducer housing containing
      a transducer horn that is connected to a signal generator and has a distal end;
      a transducer mechanism comprising a slide collar disposed around an inner ring wherein the transducer mechanism is movable from a first position to a second position wherein the second position is distal from the first position and wherein movement of the transducer mechanism from the first position to the second position engages a control ring on a catheter and moves a catheter mechanism from a first position to a second position;
and
the catheter having:
an elongated flexible body,
a proximal end,
a distal end,
a knob having a proximal end, and a distal end, wherein the elongated flexible body extends from the distal end of the knob,
the control ring disposed around the proximal end of the knob,
a nesting piece disposed within the knob near the proximal end of the knob and operatively coupled to the control ring,
at least one longitudinal lumen,
an ultrasound transmission member, having a proximal end, extending through the lumen,
a sonic connector that is secured to the proximal end of the ultrasound transmission member and disposed within the nesting piece;
and
the catheter mechanism comprising the control ring and the nesting piece that is movable from the first position that engages the nesting piece around the sonic connector restraining the sonic connector and substantially preventing the transmission of ultrasound energy and a second position that disengages the nesting piece from the sonic connector, permitting the transmission of ultrasound energy from the transducer horn to the ultrasound transmission member;
wherein the transducer housing operatively couples to the proximal end of the catheter.

2. The system of claim 1, wherein the catheter mechanism has a longitudinal interface.

3. The system of claim 1, wherein the catheter mechanism has a transverse interface.

4. The system of claim 1, wherein the sonic connector and the transducer horn have a threaded connection.

5. The system of claim 1, wherein the sonic connector and the transducer horn have a frictional connection.

6. The system of claim 1, wherein the catheter mechanism freely overlaps the sonic connector.

7. The system of claim 1, wherein the catheter mechanism comprises removable components.

8. The system of claim 1, wherein the catheter mechanism comprises fixed and removable components.

9. The system of claim 1, wherein the catheter mechanism is movable in a direction parallel to the ultrasound transmission member.

10. A method of using an ultrasound system during a medical procedure comprising:
providing an ultrasound system having:
an ultrasound transducer housing containing
a transducer horn that is connected to a signal generator and has a distal end;
a transducer mechanism comprising a slide collar disposed around an inner ring wherein the transducer mechanism is movable from a first position to a second position wherein the second position is distal from the first position and wherein movement of the transducer mechanism from the first position to the second position engages a control ring on a catheter and moves a catheter mechanism from a first position to a second position;
and
the catheter having:
an elongated flexible body,
a proximal end,
a distal end,
a knob having a proximal end, and a distal end, wherein the elongated flexible body extends from the distal end of the knob,
the control ring disposed around the proximal end of the knob,
a nesting piece disposed within the knob near the proximal end of the knob and operatively coupled to the control ring,
at least one longitudinal lumen,
an ultrasound transmission member, having a proximal end, extending through the lumen,
a sonic connector that is secured to the proximal end of the ultrasound transmission member and disposed within the nesting piece;
and
the catheter mechanism comprising the control ring and the nesting piece that is movable from the first position that engages the nesting piece around the sonic connector restraining the sonic connector and substantially preventing the transmission of ultrasound energy and a second position that disengages the nesting piece from the sonic connector, permitting the transmission of ultrasound energy from the transducer horn to the ultrasound transmission member;
and
operatively coupling the transducer housing to the proximal end of the catheter using the transducer and catheter mechanisms.

* * * * *